US005972639A

United States Patent [19]
Parandoosh

[11] Patent Number: 5,972,639
[45] Date of Patent: Oct. 26, 1999

[54] FLUORESCENCE-BASED ASSAYS FOR MEASURING CELL PROLIFERATION

[75] Inventor: Zahra Parandoosh, San Diego, Calif.

[73] Assignee: Irori, La Jolla, Calif.

[21] Appl. No.: 08/901,229

[22] Filed: Jul. 24, 1997

[51] Int. Cl.$^6$ .................................................. C12Q 1/02
[52] U.S. Cl. .................................................... 435/29
[58] Field of Search ............................. 435/6, 7.1, 7.4, 435/7.72, 21, 29, 195, 196, 375; 935/66, 76

[56] References Cited

U.S. PATENT DOCUMENTS

| | | | |
|---|---|---|---|
| 4,406,751 | 9/1983 | Blass et al. ........................... | 205/777.5 |
| 4,585,598 | 4/1986 | Harnisch ............................... | 558/196 |
| 4,614,713 | 9/1986 | Harnisch ............................... | 435/21 |
| 4,659,657 | 4/1987 | Harnisch ............................... | 435/21 |
| 4,659,671 | 4/1987 | Klibanov ............................... | 435/280 |
| 4,803,157 | 2/1989 | Sundberg et al. ..................... | 435/21 |
| 4,933,278 | 6/1990 | Connolly .............................. | 435/29 |
| 5,071,773 | 12/1991 | Evans et al. .......................... | 436/501 |
| 5,164,376 | 11/1992 | Hsu et al. ............................. | 514/45 |
| 5,166,195 | 11/1992 | Ecker .................................... | 514/44 |
| 5,210,203 | 5/1993 | Musso et al. ......................... | 548/130 |
| 5,298,429 | 3/1994 | Evans et al. .......................... | 436/501 |
| 5,354,756 | 10/1994 | Underiner et al. ................... | 514/263 |
| 5,356,797 | 10/1994 | Niesel et al. ......................... | 435/69.3 |
| 5,401,629 | 3/1995 | Harpold et al. ....................... | 435/6 |
| 5,424,440 | 6/1995 | Klem et al. ........................... | 548/114 |
| 5,436,128 | 7/1995 | Harpold et al. ....................... | 435/6 |
| 5,440,041 | 8/1995 | Leigh et al. .......................... | 544/267 |
| 5,443,986 | 8/1995 | Haughland et al. .................. | 435/4 |
| 5,489,514 | 2/1996 | Tsuji et al. ........................... | 435/69.1 |
| 5,512,438 | 4/1996 | Ecker .................................... | 435/6 |
| 5,534,524 | 7/1996 | Bonewald et al. ................... | 514/314 |
| 5,567,417 | 10/1996 | Sasisekharan et al. ............... | 424/94.5 |
| 5,576,424 | 11/1996 | Mao et al. ............................ | 536/17.9 |
| 5,578,483 | 11/1996 | Evans et al. .......................... | 435/240.2 |
| 5,589,328 | 12/1996 | Mahant .................................. | 435/4 |
| 5,597,693 | 1/1997 | Evans et al. .......................... | 435/6 |

FOREIGN PATENT DOCUMENTS

| | | |
|---|---|---|
| 9313423 | 7/1993 | WIPO . |
| 9605488 | 2/1996 | WIPO . |

OTHER PUBLICATIONS

Alam et al., Reporter genes: application to the study of mammalian gene transcription, *Anal. Biochem.* 188:245–254 (1990).

Allen et al., G–protein–coupled receptor genes as protoon-cogenes: constitutively activating mutation of the $\alpha_{1B}$–adrenergic receptor enhances mitogenesis and tumorogenicity, *Proc. Natl. Acad. Sci. U.S.A.* 88:11354–11358 (1991).

Apostol et al., Phsosphotyrosine as a substrate of acid and alkaline phsosphatases, *Acta. Biochimica Polinica* 32:187–197 (1985).

Auerbach et al., Angiogenesis inhibition: a review, *Pharmacol. Ther.* 63: 265–311 (1994).

Babson, α–Naphthyl phsophate: the preferred substrate for acid phosphatase, *Chemical Chemistry* 30: 1418–1419 (1984).

Baumgarten, A simple microplate assay for the determination of cellular protein, *J. Immunol. Methods* 82: 25–37 (1985).

Bergmeyer et al., *Methods of Enzymatic Analysis* 3d ed. vol. II, pp. 269–270, H.U. Bergmeyer, ed., Derrfield Beach, FL: Verlag Chemie, 1983.

Borefreund et al., Toxicity determined in vitro by morphological alterations and neutral red absorption, *Toxicol. Lett.* 24, 119–124 (1985).

Boyer, *The Enzymes* (3d ed.), vol. IV—Hydrolysis, pp. 373–498, New York: Academic Press, 1971.

Brauner–Osborne et al., Pharmacology of muscarinic acetylcholine receptor subtypes (m1–m5): high thoughput assays in mammalian cells, *Eur. J. Pharmacol.* 295: 93–102 (1996).

Budowle et al., An alternative, effective substrate for erythrocyte acid phsophatase phenotype detereminations, *J. Forensic Sci.* 33:915–920 (1988).

Chambers et al., Hormonal regulation of acid phosphatase release by osteoclasts disaggregated from neonatal rat bone, *J. Cell. Physiol.* 132, 90–96 (1987).

Chemiluminescent–based assays for high throughput screening, Perkin–Elmer Applied Biosystems, pp. 1–13, 1996.

Connolly et al., Determination of the number of endothelial cells in culture using an acid phsophatase assay, *Anal. Biochem.* 152:136–140 (1986).

Crouch et al., The use of ATP bioluminescence as a mesure of cell proliferation and cytotoxicity, *J. Immunol. Meth.* 160: 81–88 (1993).

Cutt, EntreMed moves into future with its angiogenesis inhibitor research program, *Genetic Engineer. News*, May 1, 1997, pp. 17, 27, 38.

de Fries et al., Quantification of mitogen induced human lymphocyte proliferation: comparison of alamarBlue® assay to $^3$H–thymidine incorporation assay, *J. Clin. Lab. Anal.* 9:89–95 (1995).

Detmar et al., Effects of recombinant tunor necrosis factor–alpha on cultured microvascular endothelial cells derived from human dermis, *J. Investig. dermatol.* 95:219S–222S (1990).

(List continued on next page.)

*Primary Examiner*—Nancy Degen
*Assistant Examiner*—Thomas G. Larson
*Attorney, Agent, or Firm*—Brown, Martin, Haller & McClain

[57] ABSTRACT

A method is for determining the number of cells in cell culture is provided. In practicing the method, the cells are lysed and incubated at about 18° C. to 25° C. at acid pH with a benzothiazole substrate for a sufficient time to generate detectable fluorescence that is proportional to cell number, and then measuring fluorescence. The method is highly sensitive and can detect small differences or changes in cell number. Thus, the method can be used in drug screening assays. An automated high throughput screening assay for identifying compounds that modulate angiogenesis using the method is also provided.

26 Claims, No Drawings

OTHER PUBLICATIONS

Eva et al., Cellular genes analagous to retroviral onc genes are transcribed in human tumour cells, *Nature* 295:116–119 (1982).

Ewen et al., Improved determination of prostatic phsop [hatse (sodium thymolphthalein monophosphate substrate), *Clin. Chem.* 22:627–632 (1976).

Fujino, Prostate and menadiol sodium diphosphate as a new substrate for measuring acid phsophatase activity and a discussion on prostatic tumor model, *Nippon Hinyokika Gakkai Zasshi* 73:507–515 (1982).

Gallati, Critical observations on the use of phenolphthalein monophosphate as a substyarte for the determination of prostatic acid phosphatase (author's translation), *J. Clin. Chem. Clin. Biochem.* 15:323–328 (1977).

Gillies, Determination of cell number in monolayer cultures, *Anal. Biochem.* 159: 109–113 (1986).

Goldberg et al., An assessment of serum acid and alkaline phsophatse determinations in prostatic cancer with a clinical validation of an acid phsophatrase assay utilizing adenosine 3'–monophosphate as substrate, *J. Clin. Pathol.* 27:140–147 (1974).

Goodwin et al., Microculture tetrazolium assays: a comparison between two new tetrazolium salts, XTT and MTS, *J. Immunol. Methods* 179: 95–103 (1995).

Gutkind et al., Muscarinic acetylcholine receptor subtypes as agonist–dependent oncogenes, *Proc. Natl. Acad. Sci. U.S.A.* 88:4703–4707 (1991).

Huschtscha et al., A rapid micro method for counting cells "in situ" using a fluorogenic alkaline phsophatase enzyme assay, *In Vitro Cell. Devtl. Biol.* 25: 105–107 (1989).

Jainchill et al., Murine sarcoma and leukemia viruses: assay using clonal lines of contact–inhibited mouse cells, *J. Virology* 4:549–553 (1969).

Julius et al., Ectopic expression of the serotonin 1c receptor and the triggering of malignant transformation, *Science* 244:1057–1062 (1989).

Kerkhof, A comparison of substrates for quantifying the signal from a nonradiolabeled DNA probe, *Anal. Biochem.* 205:359–364 (1992).

Kull et al., Estimation of cell number by neural red content: applications for proliferative and survival assays, *Appl. Biochem. Biotechnol.* 8:97–103 (1983).

Kusaka et al., Cytostatic inhibition of endothelial cell growth by the angiogenesis inhibitor TNP–470 (AGM–1470), *Br. J. Cancer* 69: 212–216 (1994).

Laughton, Quantification of attached cells in microtiter plates based on Coomassie Brilliant Blue G–250 staining of total cellular protein, *Anal. Biochem.* 140:417–423 (1984).

Lewinsohn et al., A fluorometric approach to the quantitation of cell number with application to a cell adhesion assay, *J. Immunol. Meth.* 110:93–100 (1988).

Lojda et al., Phosphates of the naphthol AS series in the quantitative determination of the alkaline and acid phossophatase activities "In Situ" studied in polyacrylamide membrane model systems and by cytospectrophotometry, *Histochemie* 11:13–32 (1967).

McCaffrey et al., A rapid fluorometric DNA assay for the measurement of cell density and proliferation in vitro, *In Vitro Cell. Devtl. Biol.* 24:247–252 (1988).

Meijer et al., The presence of low molecular weight acid phosphatase in liver tissue that cannot be demonstrated with the histochemical substarte naphthol AS–BI phsophate, *Histochemistry* 67:23–29 (1980).

Meijer et al., Evaluation of histochemical observations of activity of acid hydrolases obtained with semipermeable membrane techniques. 3. The substrate specificity of isoenzymes of acid phsophatase in m.gastrocnemius of rabbits, *Histochemistry* 60:145–153 (1979).

Messier et al., High throughput assays of cloned adrenergic, muscarinic, neurokinin, and neurotrophin receptors in living mammalian cells, *Pharamcol. Toxicol.* 76:308–311 (1995).

Morin, Ammonium thymolphthalein monophosphate as a new substrate for alkaline and acid phsophatrase determinations in serum, *Clin Chem.* 19:1135–1138 (1973).

Moses et al., Inhibitors of angiogenesis, *Biotechnology* 9:630–634 (1991).

Mosmann, Rapid colorimetric assay for cellular growth and survival: application to proliferation and cytotoxicity assays, *J. Immunol. Methods* 65:5563 (1983).

Nakayama et al., Assessment of the Alamar Blue assay for cellular growth and viability in vitro, *J. Immunol. Methods* 204:205–208 (1997).

Neumann, Substrate selectivity in the action of alkaline and acid phosphatases, *J. Biol. Chem.* 243:4671–4676 (1968).

Osawa et al., Prostatic acid phosphatase assay with self indicating substrate2,6–dichloro–4–acetylphenyl phosphate, *Clin. Chem.* 41: 200–203 (1995).

Pagliacci et al., Genistein inhibits tumour cell growth in vitro but enhances mitochondrail reduction of tetrazolium salts: a further pitfall in the use of the MTT assay for evaluating cell growth and survival, *Eur. J. Cancer* 29A:1573–1577 (1993).

Parandoosh et al., Biological evaluatiopn assay development high throughput screening, Board Report, Jan. 10, 1997.

Parandoosh, High volume synthesis and screening: two challenges that must be addressed synchrony (presentation at meeting), Advances in Labels, Signaling, and Detection, Drug Development Section, San Diego, CA, Jun. 5–6, 1997.

Paul et al., D–ephedrinephosphate, DEP: a new substrate with specificity for prostatic acid phosphatase (PAP), *Histochemistry* 56:133–145 (1978).

Pignatelli et al., Genetics andbiochemistry of collagen binding–triggered glandular differentiation in a human colon carcinoma cell line, *Proc. Natl. Acad. Sci. USA* 85:5561–5565 (1988).

Porvari et al., Site–directed mutagenesis of prostatic acid phosphatase, *J. Biol. Chem.* 269:22642–22646 (1994).

Receptor Selection Amplification Technology (R–SAT™), Receptor Technologies, Inc, 1997.

Richards et al., Measurement of cell proliferation in microculture using Hoechst 33342 for the rapid semiautomated microfluorometric determination of chromatin DNA, *Exptl. Cell Res.* 159:235–246 (1985).

Robinson et al., 4–methylumbelliferyl phosphate as a substrate for lysosomal acid phosphatase, *Biochem. Biophys. Acta* 191:183–186 (1969).

Schlager et al., Use of dyes and radioisotopic markers in cytotoxicity tests, *Meth. Enzymol.* 93:233–245 (1983).

Schulz et al., The amido black assay: a simple and quantitative multipurposes test of adhesion, proliferation, and cytotoxicity in microplate cultures of keratinocytes (HaCaT) and other cell types growing adherently or in suspension, *J. Immunol. Methods* 167:1–13 (1994).

Shawver etal., Receptor tyrosine kinases as targets for inhibition of angiogenesis, *DDT* 2:50–63 (1997).

Shimohama et al., The endogenous substrate of low molecular weight acid phosphatase in the brain is an epidermal growth factor receptor, *Brain Res.* 662: 185–188 (1994).

Stadler et al., A rapid fluorometric assay for the determination of keratinocyte proliferation in vitro, *J. Invest. Dermatol. 93*:532–534 (1989).

Suto et al., Selection of an optimal reporter gene for cell–based high throughput screening assays, *J. Biomolec. Screening 2*: 7–9 (1997).

Tsou et al., 2–hydroxy–3naphthoic acid anilide phsophate as a fluorescent histochemical substrate for phosphatase, *J. Med. Chem. 11*:1097–1099 (1968).

Van Etten et al., Substrate specificity and pH dependence of homgeneous wheat erm acid phosphatase, *Arch. Biochem. Biophys. 288*:634–645 (1991).

von Gaudecker et al., Substrate–histochemical investigations and ultrahistochemical demonstratioon of acid phsophatase in larval and prepupal salivary glands of *Drosophila melanogaster, Cell Tissue Res. 155*:75–89 (1974).

West et al., A simplified In Situ solubilization procedure for the determination of DNA and cell number in tissue cultured mammalian cells, *Analytical Biochem. 147*:289–295 (1986).

Witkowski et al., Enzyme–linked immunosorbent assay for an octapeptide based on genetically engineered fusion protein, *Anal. Chem. 65*:1147–1151 91993).

Yoshida et al., Acid phosphatases from *Fusarium moniliforme*.II. Further studies on siubstrate specificity and mode of action of acid phsophatase II, *J. Biochem. (Tokyo) 72*:49–55 (1972).

Yoshida et al., Differential endothelial migration and proliferation to basic fibroblast growth factor and vascular endothelial growth factor, *Growth factors 13*:57–64 (1996).

Page, et al., A new fluorometric assay for cytotoxicity measurements in vitro, *Intl. J. Oncology 3*:473–476, 1993.

Porstmann, et al., Qunatitaion of 5–Bromo–2–Deoxyuridine incorporation into DNA: an enzyme immunoassay for the assessment of the lymphoid cell proliferative response, *J. Immun. Meth. 82*:169–179, 1985.

Sasamoto et al. Benzothiazole derivatives as substrates for alkaline phosphatase assay with fluorescence and chemiluminescence detection. Analyst 120: 1709–1714, Jun. 1995.

FLUORESCENCE-BASED ASSAYS FOR MEASURING CELL PROLIFERATION

FIELD OF THE INVENTION

The present invention relates to assays and kits for screening compounds to identify modulators of angiogenesis. In particular, an assay for rapidly screening compounds that modulate angiogenesis is provided.

BACKGROUND OF THE INVENTION

Cell proliferation and survival are critical parameters useful for screening compounds for treatment of various disorders, including tumors and other proliferative disorders. Compounds that are selected for their ability to inhibit cell proliferation can act to (1) inhibit mitogenesis, (2) inhibit angiogenesis, or (3) activate the complement pathway and the associated killer cells.

Angiogenesis is normally observed in wound healing, fetal and embryonal development and formation of the corpus luteum, endometrium and placenta. The control of angiogenesis is a highly regulated system of angiogenic stimulators and inhibitors. Thus, angiogenesis is a critical component of the body's normal physiology, especially during wound healing.

In addition, the control of angiogenesis has been found to be altered in certain disease states, and, in many cases, the pathological damage associated with the disease is related to the uncontrolled angiogenesis. It also has a detrimental aspect, for example, when blood vessels multiply and enhance growth and metastasis of tumors. Aberrant angiogenesis is also associated with numerous disorders, including rheumatoid arthritis, where blood vessels invade the joint and destroy cartilage, and numerous ophthalmologic pathologies, such as diabetic retinopathies in which new capillaries invade the vitreous, bleed and cause blindness, and macular degeneration, prostate cancer and Kaposi's carcinoma. Angiogenesis is essential to tumor development and growth. Prevention of angiogenesis can inhibit solid tumor growth.

Compounds that have anti-angiogenic activity can be used, for example, as anti-tumor agents and for the treatment of ophthalmic disorders, particularly involving the retina and vitreous humor, and for hyperproliferative dermatological disorders, such as psoriasis, that have an angiogenic component. Thus, compounds that enhance angiogenesis and compounds that inhibit angiogenesis are being sought.

This has led to a search for specific inhibitors of endothelial cell growth. As a result, there is an interest in measuring proliferation of endothelial cells under inhibitory and stimulatory conditions as screens for discovery of inhibitors (or alternatively stimulators) of angiogenesis. Direct assessment of cell numbers, either microscopically or by particle counter is time consuming and not amenable for high throughput screening. Consequently, direct assessment has been replaced by indirect methods, such as by packed cell volume, by chemical determination of a cellular component, for example, protein or deoxyribonucleic acid, or by uptake of a chromogenic dye such as neutral red. These methods can be laborious when handling large numbers of cultures, and also inaccurate at low cell densities. For high throughput screening protocols it is necessary to rapidly and accurately measure low cell densities and/or relatively small changes in cell number over a large range of cell densities. Presently available protocols to not provide a means to do this. Thus, there is a need for convenient, rapid and reproducible assays for identifying agents that modulate angiogenesis as well as agents that modulate cell proliferation.

Therefore it is an object herein to provide a method for identifying compounds that modulate cell proliferation. In particular, it is an object herein to provide a method for screening for modulators of angiogenesis, particularly inhibitors thereof.

SUMMARY OF THE INVENTION

A method for rapidly screening for modulators of cell proliferation, particular modulators of angiogenesis, is provided. In particular, a method for measuring levels of acid phosphatase, which are indicative of cell proliferation and/or survival is provided. Thus, the method provides a means for assessing cell number in culture. The method is based on a fluorogenic enzyme assay that measures the activity of acid phosphatase. The method is particularly sensitive and, thus, is suitable for use in automated high throughput screening protocols in which small changes or differences in cell number must be detected. The method is well suited for detecting and quantifying growth of endothelial cells in culture, but is intended for assessing growth of any cells in which acid phosphatase is produced.

The method provides a highly sensitive method for determining the number of cells in culture (or the relative differences or changes in the numbers of cells in culture), and can be used to determine cell numbers as low as 50 cells.

The methods herein can be used for evaluation of cell proliferation, and by including a wash step, can be used to evaluate cell adhesion and cell killing.

In one embodiment, a rapid and accurate method for assessing endothelial cell number based on the hydrolysis of particular benzothiazole substrates by intracellular acid phosphatase is provided. The resulting fluorescent product is proportional to cell number over a large range of cell densities (from as low as 50 to as high as 20,000 or higher), and, thus, has been adapted for this purpose. The high level of fluorescence readily can be detected in an automatic fluorescence detection unit. As a result, the method is suitable for automation, and, hence for high throughput screening.

In practicing the method, the cells are lysed and incubated at about 18° C. to 25° C. at acid pH with a benzothiazole substrate for a sufficient time, generally about 45 min to 1 hour, to generate detectable fluorescence that is proportional to cell number. Fluorescence is then measured. The method is highly sensitive and can detect small differences or changes in cell number. Thus, the method can be used in drug screening assays. An automated high throughput screening assay for identifying compounds that modulate angiogenesis using the method is also provided.

The increase in sensitivity that derives from selection of these substrates, previously developed for use in assaying alkaline phosphatase is not readily apparent. All alkaline phosphatase substrates are not necessarily acid phosphatase substrates, nor is a good substrate for alkaline phosphatase necessarily a good substrate for acid phosphatase.

Reporter gene assays in which cells are transfected with a reporter gene construct containing a transcriptional control element in operative linkage with a reporter gene that encodes acid phosphatase or alkaline phosphatase are also provided. The fluorogenic substrates described herein are used to quantify the amount of acid or alkaline phosphate produced.

Previously unknown compounds and new activities for known compounds identified by the assays herein are also provided.

DETAILED DESCRIPTION OF PREFERRED EMBODIMENTS

I. Definitions

Unless defined otherwise, all technical and scientific terms used herein have the same meaning as is commonly understood by one of ordinary skill in the art to which this invention belongs. All patents and publications referred to herein are incorporated by reference.

As used herein, modulation of angiogenesis refers to the ability of a compound to inhibit or enhance the formation of blood vessels or lymph vessels. Angiogenesis (or neovascularization) is defined as the development and growth of new capillaries and blood vessels. The process of angiogenesis is essential in numerous physiological situations including the development of an embryo, normal healing of wounds and the development of the endometrium after menstruation. Apart from in those circumstances, angiogenesis in the normal adult is very rare and mitosis of the endothelial cells which generates the walls of blood vessels is very slow, with periods of cellular renewal measured in years.

Abnormal angiogenesis (that is to say stimulation of the growth of new blood vessels as a result of a pathological syndrome) is an established characteristic of numerous diseases, notably diabetic retinopathy, rheumatoid arthritis, hemangiomas and the growth of solid tumors. Angiogenesis may also play a significant part in other diseases, such as coronary artery disease and restenosis following angioplasty.

In the field of oncology it has been demonstrated that the growth of solid tumors is entirely dependent on the constant development of new blood vessels, and that development is correlated, for the metastases of certain cancers, with the growth size of the primary tumor (see, e.g., Folkman (1 971) *New J. Enal. Med.* 285:1182–1185). Angiogenesis is also required for primary solid tumor growth and metastases. An angiogenesis inhibitor may therefore stop or inhibit the growth of primary tumors, impede or reduce the formation of metastases, impede the appearance of secondary growths. Angiogenic inhibitors are also useful in the treatment of non-neoplastic disorders in which an angiogenic activity occurs.

As used herein, excitation wavelength is the wavelength of light used to generate fluorescence emission, measured in arbitrary units.

As used herein, emission wavelength is wavelength of light emitted by a fluorescent molecule after excitation.

As used herein, a control refers to an experiment in which cells are treated substantially the same as test cells, except that they are not contacted with the test compound. A control can also be one in which the cells are contacted with a known compound, such as a known inhibitor of angiogenesis of known effect.

As used herein, sensitivity of methods herein refers to the lowest number of cells that can be accurately detected. The higher signal and higher signal/background (S/N herein) by the methods herein permit lower numbers of cells to be detected.

As used herein, $K_m$ is the substrate concentration at which the rate of the enzymatic reaction is half maximal. $K_m$, thus, measures how quickly and efficiently the enzymatic reaction proceeds.

As used herein, a reporter gene construct is a DNA molecule that includes a reporter gene operatively linked to a transcriptional control sequences. Transcription of the reporter gene is controlled by these sequences. The activity of at least one or more of these control sequences is directly or indirectly regulated by the cell surface protein or an intracellular receptor. The transcriptional control sequences include the promoter and other regulatory regions, such as enhancer sequences, that modulate the activity of the promoter, or control sequences that modulate the activity or efficiency of the RNA polymerase that recognizes the promoter, or control sequences are recognized by effector molecules, including those that are specifically induced by interaction of an extracellular signal with a cell surface protein. For example, modulation of the activity of the promoter may be effected by altering the RNA polymerase binding to the promoter region, or, alternatively, by interfering with initiation of transcription or elongation of the mRNA. Such sequences are herein collectively referred to as transcriptional control elements or sequences. In addition, the construct may include sequences of nucleotides that alter translation of the resulting mRNA, thereby altering the amount of reporter gene product.

As used herein, promoter refers to the region of DNA that is upstream with respect to the direction of transcription of the transcription initiation site. It includes the RNA polymerase binding and transcription imitation sites and any other regions, including, but not limited to repressor or activator protein binding sites, calcium or cAMP responsive sites, and any such sequences of nucleotides known to those of skill in the art to alter the amount of transcription from the promoter, either directly or indirectly.

As used herein, a promoter that is regulated or mediated by the activity of a cell surface protein or receptor is a promoter whose activity changes when a cell is exposed to a particular extracellular signal by virtue of the presence of cell surface proteins and receptors whose activities are affected by the extracellular protein. For example, the c-fos promoter, which is specifically activated upon the specific interaction of certain extracellular signals, such as growth hormones, with a cell surface protein, such as a growth hormone receptor. In particular, the regulation of such promoters by the cell surface protein, though indirect, occurs within minutes of the interaction of the cell surface protein with the extracellular signal.

As used herein, operative linkage refers to a DNA fragment, such as linkage of a promoter to a DNA molecule that is transcribed by RNA polymerase that binds to the promoter, such that the regulatory region is properly positioned for its activity. Thus, a DNA fragment in operative linkage with a promoter is downstream, with respect to the direction of transcription, from the promoter, is in the correct reading frame with respect to the transcription initiation site and is inserted in a manner such transcription elongation proceeds through the DNA fragment.

As used herein, recombinant cells include any cells that have been modified by the introduction of heterologous DNA. Control cells include cells that are substantially identical to the recombinant cells, but do not express the one or more of the proteins encoded by the heterologous DNA or that do not contain a reporter gene construct. For example, the recombinant cells have are produced from cells by the introduction of DNA that encodes are reporter gene construct and also heterologous DNA encoding a cell surface receptor. Control cells, with respect to such recombinant cells, are cells that either do not include or express the reporter gene construct or that do not include or express the receptor.

As used herein, heterologous DNA includes DNA that does not occur naturally as part of the genome in which it is present or which is found in a location or locations in the genome that differs from that in which it occurs in nature. Heterologous DNA is not endogenous to the cell into which it is introduced, but has been obtained from another cell. Generally, although not necessarily, such DNA encodes RNA and proteins that are not normally produced by the cell in which it is expressed. Heterologous DNA may also be referred to as foreign DNA. Any DNA that one of skill in the art would recognize or consider as heterologous or foreign to the cell in which is expressed is herein encompassed by heterologous DNA. Examples of heterologous DNA include, but are not limited to, DNA that encodes receptors, reporter genes, transcriptional and transnational regulatory sequences, selectable or traceable marker proteins, such as a protein that confers drug resistance.

As used herein, cell surface proteins include molecules that occur on the surface of cells, interact with the extracellular environment, and transmit or transduce the information regarding the environment intracellularly in a manner that ultimately modulates transcription of specific promoters, resulting in transcription of specific genes.

As used herein, intracellular receptors are those, such as glucocorticoid receptors, that traffic in the cell.

II. Assays

The methods provided herein, are well-suited for identifying compounds that modulate cell growth and proliferation. Accordingly, a highly sensitive readily automatable method for identifying modulators, particularly inhibitors of cell growth, and more particularly inhibitors, of angiogenesis is provided.

The methods are measure intracellular acid phosphatase by reaction with benzothiazole substrates, described below. The method is suitable for use with any cells that have acid phosphatase. Cells that are known to have an acid phosphatase content and, therefore, are readily adaptable to the methods provided herein, include, but are not limited to liver, spleen, prostate gland, endothelial cells, fibroblasts and hybridoma cells.

A. The Substrate

The substrates intended for use herein are benzothiazole derivatives that have a linked fluorescence inhibiting group. These substrates are described in U.S. Pat. No. 5,424,440 for measuring alkaline phosphatase. The substrates, which are substantially non-fluorescent, have formulae:

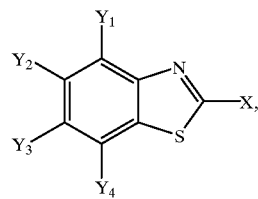

where:
at least one of $Y_1$, $Y_2$, $Y_3$ and $Y_4$, preferably $Y_3$, is —A—W and the others are hydrogen in which A is an ionizable anion group and W is a fluorescence inhibiting group, A and W are linked by a bond that is cleavable by acid phosphatase (or in instances in which a alkaline phosphatase is encoded by a reporter gene, alkaline phosphatase); and X is a chemical moiety, preferably —O—P(O)(OH)$_2$, that contains at least two atoms that extends the resonance of the benzothiazole ring, with the proviso that X is not optionally substituted thiazolyl, whereby upon cleavage of the bond between the anion group and the fluorescence inhibiting group by the phosphatase yields a product that is strongly fluorescent.

These substrates, which were designed for use in detecting alkaline phosphatase, are herein shown to be advantageously used for quantifying acid phosphatase. In fact, the level of fluorescence obtained is far greater than using other fluorescent substrates, such as 4-methylum-belliferyl phosphate (MUP), which has previously been used in assays (see, e,g., U.S. Pat. No. 5,534,524) for acid phosphatase.

It is shown herein that the substrates described herein and others of this class of compounds are substrates for acid phosphatase at acid pH, preferably between about 4.5 and up to 7, more preferably about 5 and about 6.5, and most preferably between about 6 and 6.5, inclusive. The optimum pH can vary with cells that are being assayed, since acid phosphatases from different sources will exhibit different pH maxima. Accordingly, the optimum pH for each cell type can be determined empirically. These substrates include: 2-carbamoyl-6-hydroxybenzo-thiazole phosphate (ABTP), 2'(2-benzothiazoyl)-6'-hydroxy-benzthiazole phosphate (BBTP) and 2-cyano-6-hydroxybenzothiazole phosphate (CBTP), as follows:

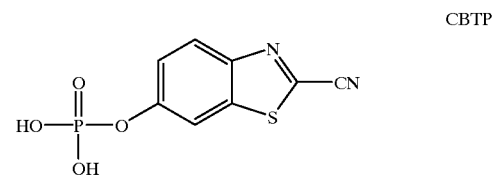

CBTP

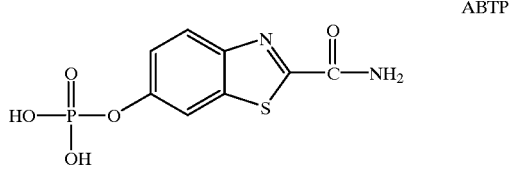

ABTP

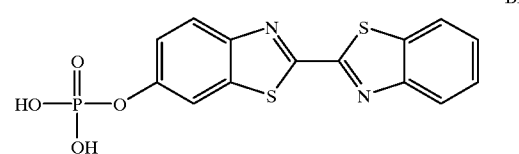

BBTP

The products of the reactions catalyzed by the enzyme are:

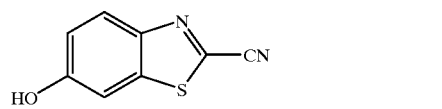

CBT

ABT

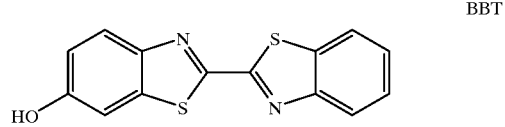

BBT

The preferred compound is 2'[2-benzothiazoyl]-6'-hydroxy-benzthiazole phosphate, preferably the bis[2-amino-2-methyl-1,3-propanediol] salt. BBTP is sold under the trademark ATTOPHOS™ (JBL Scientific, InC. (San Luis Obispo, Calif.). ABT, CBT and BBT are fluorescent in a basic aqueous solution from 445 nm–580 nm (ABT and CBT) and 460 nm–660 nm (BBT) with maximum emission at 510, 518 and 561 nm, respectively. The excitation occurs over a range from 320 nm–430 nm (CBT), 325–440 nm (ABT) and 330–480 nm (BBT), with the maximum at 381, 381 and 419 nm, respectively.

The reaction, catalyzed by alkaline phosphatase at pH 9.8 to 10 is, with reference to BBTP, as follows:

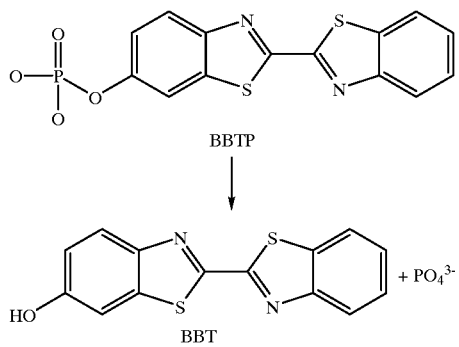

BBTP

↓

BBT + $PO_4^{3-}$

As shown herein, these substrates can be used to assay for acid phosphatase, and provide the basis for highly sensitive fluorescence based assays to detect cell proliferation.

B. Acid Phosphatase

Previously, the level of acid phosphatase has been monitored using UV visible spectrophotometry, radioimmunoassay (RIA), and the commonly available fluorescent substrate 4-MUP; none of the substrates provided sufficient sensitivity or reliability for automated drug screening assays. A distinction between acid and alkaline phosphatases is based upon the marked difference in the pH ranges in which these enzymes are active. This, however, is not the only distinction between these types of enzymes. There are profound differences in their substrate specificities (see, e.g., Neumann (1968) *J. Biol. Chem.* 243:4671–4676). For example, O-substituted derivatives of nucleotides of phosphorotic acid are hydrolyzed by acid phosphatase, but are not susceptible to hydrolysis by acid phosphatase. The array of competitive inhibitors for each enzyme are vastly different (see, e. g., Hollander (1971), Chapter 19, p.463 in *The Enzymes*, Vol. IV, ed. Boyer, P. D., Academic Press, N.Y., compared with Reid et al., (1971) Chapter 17, p.395, in *The Enzymes*, Vol. IV, ed. Boyer, P. D., Academic Press, N.Y.).

To illustrate these differences the following Tables (from Hollander (1971), Chapter 19, pp.449–498 in *The Enzymes*, Vol. IV, ed. Boyer, P. D., Academic Press, N.Y.) are provided.

TABLE I

HYDROLYSIS PRODUCTS OF VARIOUS O- AND S-SUBSTITUTED MONOESTERS OF PHOSPHOROTHIOIC ACID BY ALKALINE AND ACID PHOSPHATASES[a]

| Substrate | Alkaline phosphatase, products identified[b] | Acid phosphatase, products identified[c] |
|---|---|---|
| Cysteamine S-phosphate | Cysteamine, $^{32}P_i$ | No cleavage |
| N-Acetylcysteamine S-phosphate | N-Acetylcysteamine, $^{32}P_i$ | No cleavage |
| S-(Carboxymethyl) phosphorothioate | d, $^{32}P_i$ | No cleavage |
| S-[2-(Methoxycarboxyl)ehtyl] phosphorothioate | d, $^{32}P_i$ | No cleavage |

TABLE I-continued

HYDROLYSIS PRODUCTS OF VARIOUS O- AND S-SUBSTITUTED MONOESTERS OF PHOSPHOROTHIOIC ACID BY ALKALINE AND ACID PHOSPHATASES[a]

| Substrate | Alkaline phosphatase, products identified[b] | Acid phosphatase, products identified[c] |
|---|---|---|
| O-Methyl phosphorothioate | No cleavage | $^{35}$S-Phosphoro-thioate, d |
| O-Ethyl phosphorothioate | No cleavage | $^{35}$S-Phosphoro-thioate, d |
| O-p-Nitrophenyl thiophosphate | No cleavage | $^{35}$S-Phosphoro-thioate, p-nitrophenol |
| p-Nitrophenyl phosphate | p-Nitrophenol, $^{32}P_i$ | $P_i$, p-nitrophenol |

[a]From Neumann (1968) J. Biol. Chem. 243: 4671–4676
[b]Identical products were obtained with alkaline phosphatases from the various sources.
[c]Identical products were obtained with acid phosphatases from the various sources.
[d]The alcohol liberated was not identified.

TABLE II

ENZYMIC HYDROLYSIS OF THREE TYPES OF SUBSTRATES BY ALKALINE AND ACID PHOSPHATASES[a]

| Enzyme and substrate | Cleavage shown by high voltage paper, electrophoresis | V max[b] | $K_m$ (M) |
|---|---|---|---|
| Alkaline phosphatase (*E. coli*) | | | |
| Cysteamine S-phosphate | Yes | $4.2 \times 10^{-8}$ | $9.4 \times 10^{-5}$ |
| p-Nitrophenyl phosphate | Yes | $5.8 \times 10^{-8}$ | $9.4 \times 10^{-5}$ |
| p-Nitrophenyl thiophosphate | No | | |
| Alkaline phosphatase (intestinal) | | | |
| Cysteamine S-phosphate | Yes | $0.7 \times 10^{-8}$ | $2.5 \times 10^{-4}$ |
| p-Nitrophenyl phosphate | Yes | $1.1 \times 10^{-8}$ | $2.5 \times 10^{-4}$ |
| O-p-Nitrophenyl thiophosphate | No | | |
| Acid phosphatase (potato)[c] | | | |
| Cysteamine S-phosphate | No | | |
| p-Nitrophenyl phosphate | Yes | $5.2 \times 10^{-10}$ | $2.5 \times 10^{-4}$ |
| O-p-Nitrophenyl thiophosphate | Yes | $3.2 \times 10^{-10}$ | $2.2 \times 10^{-4}$ |

[a]Neumann (1968) J. Biol. Chem. 243: 4671–4676
[b]Maximum rates of hydrolysis, $V_{max}$, were expressed as moles of substrate hydrolyzed per ml per min per μg of enzyme per ml of reaction mixture. The reactions were followed by spectrophotometric determination of the products.
[c]Essentially identical results were obtained with acid phosphatase preparations from wheat germ and from bovine prostate gland.

Thus, there are fundamental differences between the two enzymes. A good substrate for one enzyme will not necessarily be a good substrate or even a substrate for the other.

Other than for the reporter gene assays discussed below, acid phosphatase is of interest herein. It was discovered that the benzothiazole substrates described herein can serve as efficient substrates for acid phosphatases (km≈100 μM for BBTP, see EXAMPLES). Based on this high efficiency and the high signal that is generated, the assays described herein were developed.

C. Proliferation Assay

The methods herein are particularly adaptable to determination of cells in small numbers such as in microwell tissue culture plates. These plates typically 96 wells per plate, but higher density formats are available, including the 96 well half area format, and 384 well plates, and can accommodate as little as a fraction of a milliliter of cells or cell lysate per well, for example, 0.2 ml or less, containing as few as 50 cells. Use of such plates are advantageously adaptable to automation. Cells are introduced into the microtiter tissue culture plates or other suitable vessels. The cells are allowed to adhere and are then incubated under lysing conditions (i.e., in buffer with detergent, such as TRITON X-100 or SDS) with the benzothiazole substrates. Alternatively, the cells can be lysed prior to addition of the substrate. In such instances the cells can be lysed by adding appropriate buffer or by mechanical disruption or other methods known to those of skill in this art. The vessels, particularly the microtiter plates, and can be placed in commercially available instruments for measuring fluorescence, such as the Fluoroskan II, which can be interfaced with a computer for data analysis and the Cytofluor 4000, PerSeptive Biosystems. The method may also employ suspension cultures.

In an exemplary embodiment, human endothelial cells, which grow adherently, were cultured to confluence in 96-well plates. The correlation between cell number and acid phosphatase activity in each microwell was examined with cells freshly harvested from culture. Determined numbers of cells were inoculated into gelatin coated wells, cells were allowed to attach and the level of acid phosphatase was measured using p-nitrophenol phosphate (p-NPP), 4-methylumbelliferyl phosphate (MUP or 4-MUP), and BBTP. The results showed a linear relationship between cell number and enzyme activity, but the range of linearity varied substantially.

With p-NPP the curve is bi-phasic and the minimal number of cells that could be determined was only at best about 5000 cells (and only with incubation at 37° C.) and with MUP it was at best about 1000. With BBTP, however, the minimal number of cells that could be accurately determined was as low as 50. Thus, use of BBTP as a substrate in this assay, generates lower background, higher signal, and greater sensitivity, which is necessary for quantitative assays.

By optimizing the conditions for a selected cell type for assaying with BBTP, the assay can be adapted for screening large numbers of test compounds to identify inhibitors or stimulators of cell proliferation. To demonstrate this, a large range of cell densities were plated onto 96-well plates, and after incubation in assay solution (containing the BBTP) for various time intervals, fluorescence was measured. After 60 min, it was found that an accurate discrimination between various cell densities was obtained with a highly significant correlation coefficient of 0.9 between relative fluorescence units and cell number. In preferred embodiments, after adherence of the cells and before the assay, the plates are washed to remove dead cells. Comparison of numbers with and without a wash will also provide an estimate of adherent cells. If the cells are treated with an agent whose cytotoxicity is being assess, this comparison will indicate cell death.

A similar experiment was performed using human dermal microvascular endothelial cells, and a linear correlation between cell number and relative fluorescence units was observed. The optimum pH for the reaction was about pH 6.5, and an apparent $K_m$ on the order of about 100 $\mu$M substrate [see, EXAMPLE 3] was determined. In contrast, the $K_m$ of the substrate with alkaline phosphatase is reported to be on the order of about 2 mM (see, U.S. Pat. No. 5,424,440). From this data, it appears that this substrate is used more efficiently by acid phosphatase than alkaline phosphatase.

Several cell lines were tested using BBTP as the substrate, and a linear relationship between cell number and relative fluorescence units was observed. The range of linearity varied for different cell types as well as the $K_m$ for the various acid phosphatases and BBTP. Cells that were tested included NIH 3T3 fibroblast cells, chinese hamster ovary cells (CHO-K1), human epidermoid carcinoma cells (A431) and human ovarian carcinoma cells (2008). The results of the these experiments are set forth in the EXAMPLES The results demonstrate that the method herein can be adapted for use with a wide variety of cell types, and, can, thus be used for any purpose in which cell proliferation is measured. Because of the high sensitivity of the method, it is particularly adaptable for use in assays for screening for compounds that modulate (alter) cell proliferation (drug screening assays). Inhibitors of proliferation will be useful for treating pathologies that derive from cell proliferation, such as tumors, diabetic retinopathies, arthritis and other such disorders described herein. Identification of stimulators of cell proliferation is also of interest as a means to identify transformation factors.

D. Drug Screening Assay

In order to screen compounds for activity as inhibitors or stimulators (i.e., modulators) of cell proliferation, a method that reliably and accurately measures high and low numbers in the same setting (i.e., the same plate). Because typically, when performing these assays, some cells are treated with a test compound, and control cells are untreated, the control cells will grow to relatively high numbers. Treated cells, when the test compound is an inhibitor, will be present at low numbers. Thus, there is a need to see low numbers of cells as well as the high numbers in the controls. Thus, both ends (high and low cell densities) must be in the same linear range.

Also, by virtue of the high sensitivity and high signal that is generated, the process can be miniaturized by using smaller wells, fewer cells, and less reagent.

Because the methods herein can reliably and sensitively detect small changes or differences in cell number and low cell numbers and high cell numbers throughout a linear range, they can be used in drug screening assays. Accordingly, methods for screening test compounds to identify those that inhibit or stimulate cell proliferation are provided.

In an exemplary embodiment, the method is practiced with endothelial cells, which are involved in angiogenesis. Thus, in particular embodiments, methods for screening test compounds that modulate angiogenesis are provided. It is understood, however, that the method may be practiced with any cell type known or determined (by methods, such as those demonstrated herein) to express acid phosphatase in an amount that can be correlated with cell number.

For screening compounds for activity as angiogenesis inhibitors:

endothelial cells are plated onto suitable substrate (typically plate 500 cells, since the method will detect as low as 50 cells), preferably 96-well or half area 96-well plates, allowed to adhere;

test compounds can be added to the cells at this point or after stimulation of proliferation;

after about a sufficient time, typically between about 0.5 to 2.0 hours, cells are stimulated to proliferate by addition of known proliferation agents, such as growth factors, including acidic fibroblast growth factor (FGF), basic FGF, epidermal growth factor (EGF), vascular endothelial growth factor (VEGF), or any other agent known to those of skill in the art;

cells are incubated for a suitable time, typically about one to about three days, and acid phosphatase is measured.

To measure acid phosphatase, medium is removed, such as by vacuum aspiration, and dead cells are removed from each well, such as by washing with a suitable buffer, such as phosphate buffered saline (PBS). The benzothiazole substrate, preferably BBTP, described herein is added in a suitable buffer, preferably in a lysing buffer at acidic pH (about 5 up to about 7, preferably about 5 up to and including about 6.5, containing a detergent, such as TRITONX-100) to each well. Suitable buffers include, for example, 0.1 Tris citrate (0.1 Tris-base, 0.1 M citric acid, pH 6.5, containing 0.25% Triton X-100). The plate is shaken, such as on an orbital shaker, for a time sufficient to lyse the cells and for the enzyme catalyzed cleavage of substrate to occur, about 1 to 10 min preferably about 5 min. The reaction is stopped by raising the pH above about 7, by adding, for example, diethanolamine, pH 10.0. Fluorescence is measured at a suitable excitation wavelength (about 450 nm if the substrate is BBTP) and emission (580 nm if the substrate is BBTP) using a fluorimeter (e.g., Cytofluor 4000, PerSeptive Biosystems). Backgrounds for nonenzymatic hydrolysis is determined in wells containing no cells, and is subtracted from experimental values.

When screening for compounds that stimulate angiogenesis are being sought, the step of adding a known stimulator of angiogenesis is not included.

These assays are preferably formatted for high throughput screening using high density microplates and suitable automated equipment for measuring fluorescence (see, e.g., International PCT application Nos. WO 93/13423 and WO 96/5488).

E. Reporter Gene Assays and other Assays of Alkaline Phosphatase

Reporter gene assays have numerous applications in which levels of expression of a gene operatively linked to an inducible promoter are measured. This technology was originally used to study gene expression and regulation, and is well-suited for studying receptor function and activity. It has since been extended to the drug discovery process for characterization of receptor function, and metabolic regulation. A reporter gene construct contains an inducible transcriptional control element operatively linked for expression to a reporter construct. The functional reporter response is used to select for compounds in high throughput screening protocols. Among the commonly used reporter genes are those encoding secreted alkaline phosphatase, which is a mutated form of placental alkaline phosphatase. Since endogenous alkaline phosphatase is not secreted, it does not interfere with the reporter signal. Clontech presently markets vectors and reagents for fluorescent alkaline phosphate assays using MUP as a substrate. These assays are 10-fold to 100-fold less sensitive than chemiluminescence-based assays for alkaline phosphatase. In the methods provided herein, the benzothiazole substrates described herein, particularly BBTP, are used in place of MUP. The resulting assays are significantly more sensitive than the assays using MUP.

The most commonly described reporter gene assays use chloramphenicol acetyl transferase, β-galactosidase, luciferase, B-glucuronidase and secreted alkaline phosphatase (Alam et al. (1 990) Anal. Biochem. 188:245–254). Of interest herein are those assays in the enzyme alkaline phosphatase or acid phosphatase is expressed. The methods herein are used to detect and/or quantify such enzymes.

In a reporter gene assay, a reporter gene construct is linked to a transcriptional control element that responds to a transduced signal or to a regulatory molecule, and, thus can assess receptor function, modulators of receptor activity or other such parameters. Such assays are well known (see, e.g., U.S. Pat. No. 5,589,328, 5,512,438, 5,489,514, 5,356, 797, 5,164,376, 5,166,195, 5,354,756, 5,440,041, 5,597,693, 5,578,483, 5,298,429, 5,071,773, 5,401,629, 5,436,128). These assays are used, for example, for screening for modulators of the activity of cell surface proteins and also intracellular receptors, or for identifying receptors and assessing receptor activity. DNA encoding secreted alkaline phosphatase is among the more commonly used reporter genes. Upon activation of the transcriptional control element, the gene is expressed and alkaline phosphatase is expressed and secreted into the medium. As provided herein, the benzothiazole substrates are used in reactions that quantify the secreted alkaline phosphatase.

In the embodiments herein, a reporter gene assay in which DNA encoding alkaline phosphatase or acid phosphatase is used as the reporter gene, and the activity is assessed using the benzothiazole substrates described herein to measure alkaline phosphatase or acid phosphatase activity is provided. When alkaline phosphatase activity is measured, the pH of the reaction mixture is greater than 7, preferably about 7 to 10, more preferably between about 8 and 10, and more preferably between about 9 and 10.

F. Practice of the Assays

As noted above, the method is based on the detection of acid phosphatase in cells, which method is known to those of skill in the art (see, e.g., U.S. Pat. No. 4,933,278, see, also Connolly et al. (1986) Anal. Biochem. 152:136–140) for detection of acid phosphatase in endothelial cells. In implementing that method, in order to generate a signal sufficient to detect low numbers of cells, requires at least a 2 hour incubation. Furthermore, the curve of cell number versus O.D. is biphasic. As a result, small changes in cell number and low cell densities cannot be detected, since the control value in which cells are untreated, is not directly comparable to test value.

The modification herein in which the benzothiazole derivative substrates, described for alkaline phosphatase, are used in place of p-nitrophenyl phosphate, provides a substantial improvement in sensitivity and reliability. Because of this increase in sensitivity, the method herein can be used with a variety of cell types and for detection of very small changes or differences in cell number.

The determination of the number of cells can be made at any convenient time during the cell culture period in which it is desired to follow the growth or survival of the cells. These cells can be growing in conventional tissue culture flasks such as, for example, T-flasks, roller bottles, flat bed chambers, hollow fiber reactors, agitated suspension culture vessels and the like cell culture devices under various suspension or anchorage-dependent cell culture conditions. Preferred devices are microtiter plates designed for use with high throughput automated instrumentation. The time and frequency of the cell counts will depend upon the nature of the specific cells being cultured, their normal growth period, the cell products sought after and other such factors. By following the cell count, one can readily determine the growth phase or stage in which the cells exist at any given time. Since non-adherent cells and dead cells will be removed when washed, the methods can be used to measure cell adhesion when the cells are cultured under anchorage-dependent conditions.

Incubation is preferably carried out at pH and temperature conditions of maximum enzyme activity. The acid phosphatases have optimal activity at acid pH and the preferred range used herein is from about 4.5 up to about 7, preferably about 4.5 to about 6.5, inclusive, more preferably about 5.5 to 6.5 inclusive. The preferred temperature range is from about 18° C. to about 25° C., although higher temperatures, up to about 37° C. can be used. In preferred embodiments, about 50 $\mu$M to 1 mM, preferably about 100 to about 500 $\mu$M concentrations of substrate are used. Following incubation for a predetermined period of tune, typically 30 min up to about 2 hour, preferably about 30 min to about 1 hour, more preferably about 45 min to 1 hour, the enzymatic reaction is stopped by any suitable means, preferably by raising the pH above 7 to preferably between 8 and 11, more preferably between about 9 and 10, by addition of alkali, such as NaOH. The fluorescence produced by the cells is then measured by exposing the cells to an excitation wavelength (450 nm the preferred substrate BBTP) for the substrate and detecting fluorescence at an emission wavelength (580 nm for BBTP).

Thus, the method herein includes the steps of lysing cells, incubating the cell lysate with the benzothiazole substrate, preferably, BBTP, at acidic pH (typically 4.5 up to 7, preferably 4.5 to 6.5, more preferably 5.5 to 6.5) at, preferably about room temperature (18° C.–25° C., preferably about 20° C.) and then measuring fluorescence.

Cell number can by determined by comparing the fluorescence produced to a control curve developed using identical conditions, but known numbers of cells. Such curve can be developed, for example, by determining the number of cells per well or other unit of cells in at least three different levels and plotting against fluorescence to form a straight line relationship. The number of cells for any cell culture of the given cells can then be estimated by carrying out the method and the comparing fluorescence to a control curve. In automated methods, such data can be included in the programming of the instrument and cell number determined automatically.

For reporter gene assays, recombinant cells that contain a reporter gene construct in which the reporter gene is secreted alkaline phosphatase are used. The cell supernatant is transferred to a suitable vessel, preferably a well of a microtiter plate, reaction buffer, which includes the benzothiazole substrate is added, the reaction mixture is incubated for a sufficient time (typically 45 min to one hour or less), and fluorescence is measured.

III. Kits and Diagnostic Systems

The assay systems herein may be provided in kit form that is useful for detecting the acid phosphatase activity. In particular, kits for performing the assays herein are also provided. In particular, kits for measuring acid phosphatase activity are provided. These kits contain a first reagent containing the substrate. The kits may also include suitable ancillary reagents, such as the appropriate buffers, such as diethanolamine and borate buffer, at a pH appropriate for stopping the reaction, typically between about 7 and about 11.5, preferably, 7 to 11, or 7 to 10.5 or 7.5 to 10, catalyzed by acid phosphatase depending upon the enzyme. The kits may also include suitable ancillary supplies, such as microtiter plates, vials, calibrator solutions, controls, wash solutions, solid-phase supports and the like.

The packages discussed herein in relation to diagnostic systems are those customarily utilized in diagnostic systems. Such packages include glass and plastic, such as polyethylene, polypropylene and polycarbonate, bottles and vials, plastic and plastic-foil laminated envelopes and the like. The packages may also include containers appropriate for use in auto analyzers. The packages typically include instructions for performing the assays.

The following examples are included for illustrative purposes only and are not intended to limit the scope of the invention.

EXAMPLE 1

Experimental Design and Methods

Materials
Cells lines and cultures
Human endothelial cells (human dermal microvascular (HDMEC) and human umbilical vein (HUVEC) were obtained from Clonetics. Primary cultures were maintained in flasks (Corning) containing endothelial cell growth medium (Clonetics) supplemented with 10% fetal bovine serum (FBS, Sigma), bovine brain extract (12 μ/mL), hydrocortisone (1 μ/mL), human epidermal growth factor (10 ng/mL), gentamicin sulfate (50 μ/mL), and amphotericin-B (50 ng/mL). Passages 3–7 were used in experiments.

CHOK-1 and 3T3 cells were obtained from the American Type Tissue Culture Collection, Rockville, Md. CHK-1 cells were maintained and cultured in HAM's F12 supplemented with 10% FBS. 3T3 cells were grown in DMEM supplemented with 10% FBS, 2 mM L-glutamine and nonessential amino acids.

Chemicals
p-Nitrophenyl phosphate was obtained from Sigma. 4-Methylum-belliferyl phosphate (MUP) was obtained from Molecular Probe and 2'-[2-benzthiazoyl]-6'-hydroxybenzthiazole phosphate bis-[2-amino-2-methyl-13-propanediol] salt (AttoPhOS™) was purchased from JBL Scientific Inc. All other chemicals were obtained from Sigma.

Methods
Measurement of cell number using acid phosphatase assay.

To establish a relation between acid phosphatase activity and cell numbers, cells were seeded at various densities (50–20,000) onto replicate plastic 96-well plates or half area 96-well microtiter plates (Costar) and incubated at 37° C. for 3.5 hours to allow attachment. Cell number was then assessed by measuring intracellular acid phosphatase with three different substrates: p-nitrophenyl phosphate, which has a calorimetric endpoint, 4-methylumbelliferyl phosphate (MUP) and 2'-[2-benzthiazoyl]-6'-hydoxybenzothiazole phosphate bis-[2-amino-2-methyl-13-propanediol] salt (AttoPhos™), which have fluorometric endpoints.

EXAMPLE 2

Results Using Various Substrates
A. p-nitrophenyl phosphate (p-NPP).

At the end of the incubation period the medium was removed by vacuum aspiration and each well was washed once with Dulbecco's phosphate buffered saline (D-PBS). To each well 100 μL of assay buffer (100 mM sodium acetate, pH 5.5, containing 0.1% Triton X-100 and 100 mM p-NPP) was added and the plates were incubated at 37° C. for 1 hour. At the end of incubation the reaction was stopped by the addition of 10 μL 1 M sodium hydroxide, and color development was determined at 405 nm using a microplate reader (Molecular Devices). Nonenzymatic hydrolysis was determined in wells containing no cells and subtracted from the experimental values.

TABLE 1

Evaluation of acid phosphatase activity of the HUVEC by p-NPP in 96-well plate

| HUVEC/well of 96-well plate | Optical Density 405 nm |
| --- | --- |
| Background | 0.21 ± 0.07 |
| 50 | 0.21 ± .003 |
| 100 | 0.208 ± .002 |
| 250 | 0.213 ± .009 |
| 500 | 0.216 ± 002 |
| 1000 | 0.221 ± .008 |
| 2500 | 0.248 ± .006 |
| 5000 | 0.287 ± .004 |
| 7500 | 0.305 ± .002 |
| 10000 | 0.345 ± .004 |
| 15000 | 0.415 ± .006 |
| 18000 | 0.455 ± .002 |
| 20000 | 0.476 ± .008 |

The relationship between cell number and O.D. is non-linear at low densities, consequently with a 1 hour incubation fewer than about 5000 cells cannot be detected. If the reaction is permitted to go longer, i.e. 2 hours, then curve is biphasic so that at a higher number of cells, the proportionality between enzyme concentration and cell number is different from that a low cell number. Therefore, this calorimetric assay is unsuitable for detecting low numbers of cells and/or small changes is cell growth. In addition, at room temperature the reaction is slower and the non-linear effects are magnified. Thus, this assay is cannot be used for rapid high throughput methods. Other experiments demonstrated that the minimal number of cells detected under these conditions (varying time) with these cells is about 5000.

B. 4-methylumbelliferyl phosphate (MUP)

After washing with D-PBS, 25 μL lysis buffer (100 mM Tris-citrate, pH 6.5 containing 0.2% Triton X-100) was added to each well. Plates were incubated at room temperature for 5 minutes on an orbital shaker at speed 300, after which 75 μL MUP in Tris-citrate acetate was added to each well. Plates were incubated for 1 hour at room temperature and the reaction was terminated with 50 μL of stop solution (150 mM NaOH, pH 9).

Fluorescence was measured at an excitation wavelength of 360 nm and emission wavelength of 460 nm using a fluorimeter (Cytofluor 4000, PerSeptive Biosystems). Nonenzymatic hydrolysis was determined in wells containing no cells and subtracted from the experimental values. Signal linearity was maintained throughout cell density range.

TABLE 2

Evaluation of acid phosphatase activity of the HUVEC by MUP in 96-well plate

| HUVEC/ well | MUP concentration (μM) | | | | | |
|---|---|---|---|---|---|---|
| | 100 | | 250 | | 500 | |
| 96-well plate | Fluorescence[t] | *S/N | Fluorescence | *S/N | Fluorescence | *S/N |
| Background | 32 ± 15 | — | 27 ± 6 | — | 58 ± 6 | — |
| 1,000 | 21 | N/A | 67 ± 2 | 2.5 | 144 ± 21 | 2.5 |
| 2,000 | 83 ± 13 | 2.6 | 167 ± 10 | 6.2 | 444 ± 21 | 7.7 |
| 4,000 | 191 ± 11 | 8.6 | 523 ± 90 | 19.4 | 1049 ± 79 | 18.1 |
| 8,000 | 438 ± 10 | 13.7 | 1049 ± 47 | 38.9 | 2335 ± 199 | 40.3 |
| 16,000 | 981 ± 110 | 30.7 | 2188 ± 217 | 81 | 4449 ± 394 | 76.7 |

*denotes signal-to-noise ratio
[t]fluorescence throughout the Examples is measured in relative fluorescence units (RFU)

Using MUP low cell numbers and small changes are barely detectable. Although linearity was observed, the signal was relatively low.

C. 2'-[2-benzthiazoyl]-6'-hydroxybenzthiazole phosphate bis-[2-amino-2-methyl-13-propanediol] salt (AttoPhos™)

After washing with D-PBS, 150 μL 0.5 mM AttoPhos™ in 0.1 M Tris-citrate (0.1 M Tris-base, 0.1 M citric acid, pH 6.5 containing 0.25% Triton X-100) was added to each well and placed on an orbital shaker for 5 minutes as described for MUP. Plates were incubated for 1 hour at room temperature and the reaction was terminated with 50 μL of stop solution (240 mM diethanolamine, pH 10). Fluorescence was measured at excitation wavelength of 450 nm and emission wavelength of 580 nm using a fluorimeter (Cytofluor 4000, PerSeptive Biosystems). Nonenzymatic hydrolysis was determined in wells containing no cells and subtracted from the experimental values. Since the background is subtracted, in general, the actual signal to noise ratios at lower cell numbers is better than what presented in the table.

TABLE 3

Evaluation of acid phosphatase activity of the HUVEC by AttoPhos ™ in 96-well plate

| | AttoPhos ™ Concentration (μM) | | | |
|---|---|---|---|---|
| HUVEC/well | 250 | | 500 | |
| 96-well plate | Fluorescence | *S/N | Fluorescence | *S/N |
| Background | 83 ± 3 | — | 78 ± 3 | — |
| 625 | 1695 ± 65 | 20 | 1561 ± 39 | 20 |
| 1,250 | 2853 ± 180 | 34 | 2737 ± 106 | 35 |
| 2,500 | 5019 ± 188 | 60 | 5186 ± 125 | 66 |
| 5,000 | 10578 ± 119 | 127 | 10406 ± 498 | 133 |
| 10,000 | 20670 ± 967 | 249 | 21198 ± 240 | 272 |
| 20,000 | 37889 ± 501 | 456 | 38528 ± 1540 | 494 |

Linearity was maintained from 625–20,000 cells per well

It can be seen that the amount of fluorescence generated use BBTP as substrate is substantially greater than that generated using MUP.

TABLE 4

Evaluation of acid phosphatase activity of the HUVEC by AttoPhos ™ in half area 96-well (A/2) plate.

| | AttoPhos ™ Concentration (μM) | | | |
|---|---|---|---|---|
| HUVEC/well | | | | |
| 96-well | 250 | | 500 | |
| A/2 plate | Fluorescence | *S/N | Fluorescence | *S/N |
| Background | 548 ± 33 | — | 606 ± 41 | — |
| 625 | 1867 ± 68 | 3.4 | 2040 ± 55 | 3.4 |
| 1,250 | 3438 ± 132 | 6.3 | 3757 ± 132 | 6.2 |
| 2,500 | 6664 ± 128 | 12.1 | 7046 ± 240 | 11.6 |
| 5,000 | 12807 ± 399 | 23.4 | 14586 ± 498 | 24 |
| 10,000 | 25684 ± 1488 | 46.9 | 28302 ± 448 | 46.7 |
| 20,000 | 46409 ± 1009 | 84.7 | 49706 ± 790 | 82 |

Linearity was maintained from 625–20,000 cells per well.

TABLE 5

Evaluation of acid phosphatase activity of the HDMEC by AttoPhos ™ in half area 96-well (A/2) plate.

| HDMEC/well 96-well A/2 plate | AttoPhos ™ Concentration ($\mu$M) | | | | | |
|---|---|---|---|---|---|---|
| | 100 | | 250 | | 500 | |
| | Fluorescence | *S/N | Fluorescence | *S/N | Fluorescence | *S/N |
| Background | 171 ± 72 | — | 112 ± 8 | — | 162 ± 1 | — |
| 50 | 829 ± 26 | 4.8 | 1014 ± 80 | 9.1 | 1496 ± 4.6 | 9.3 |
| 100 | 1609 ± 157 | 9.4 | 1545 ± 253 | 13.8 | 2032 ± 97 | 12.6 |
| 250 | 2347 ± 209 | 13.7 | 2383 ± 24 | 21.2 | 3686 ± 270 | 22.8 |
| 500 | 3682 ± 263 | 21.5 | 3998 ± 313 | 35.7 | 6404 ± 665 | 39.6 |
| 1,000 | 6653 ± 483 | 38.8 | 7594 ± 411 | 67.8 | 9822 ± 930 | 60.8 |
| 2,500 | 15566 ± 167 | 90.9 | 13382 ± 310 | 119.5 | 20580 ± 436 | 127 |
| 5,000 | 28018 ± 817 | 163.5 | 25468 ± 843 | 227.4 | 34112 ± 1797 | 211 |
| 10,000 | 35787 ± 1325 | 208.9 | 40725 ± 1850 | 363.6 | 54430 ± 133 | 336.7 |

Linearity was maintained from 50–10,000 cells per well

As described herein, this method may be used for assessment of numbers of cells other than endothelial cells. The following show that the method is highly sensitive using CHO-K1 and 3T3 cells.

TABLE 6

Evaluation of acid phosphatase activity of the CHO-K1 by AttoPhos ™ in half area 96-well (A/2) plate.

| CHO-K1/well 96-well A/2 plate | AttoPhos ™ Concentration ($\mu$M) | | | | | |
|---|---|---|---|---|---|---|
| | 100 | | 250 | | 500 | |
| | Fluorescence | *S/N | Fluorescence | *S/N | Fluorescence | *S/N |
| Background | 92 ± 6 | — | 116 ± 8 | — | 147 ± 19 | — |
| 250 | 552 ± 26 | 6 | 683 ± 36 | 5.9 | 721 ± 90 | 4.9 |
| 500 | 790 ± 70 | 9 | 1008 ± 21 | 8.7 | 1010 ± 126 | 6.9 |
| 1,000 | 1031 ± 138 | 12.3 | 1296 ± 64 | 11.2 | 1400 ± 47 | 9.5 |
| 2,000 | 2179 ± 156 | 23.7 | 2628 ± 148 | 22.7 | 2936 ± 382 | 20 |
| 4,000 | 3905 ± 234 | 42.4 | 4162 ± 122 | 35.9 | 4832 ± 357 | 32.9 |
| 8,000 | 7785 ± 684 | 84.6 | 8356 ± 237 | 72 | 9138 ± 440 | 62.2 |
| 12,000 | 12481 ± 462 | 136 | 12959 ± 124 | 111.7 | 12198 ± 83 | 83 |

TABLE 7

Evaluation of acid phosphatase activity of 3T3 cells by AttoPhos ™ in 96-well plate.

| 3T3 cells/well 96-well plate | AttoPhos ™ (500 $\mu$M) | |
|---|---|---|
| | Fluorescence | S/N |
| Background | 201 ± 23 | — |
| 250 | 1866 ± 100 | 9.3 |
| 500 | 3194 ± 172 | 16 |
| 1,000 | 6149 ± 176 | 30.7 |
| 2,000 | 10115 ± 840 | 50.6 |
| 4,000 | 21314 ± 1558 | 107 |
| 8,000 | 44831 ± 1793 | 224 |
| 10,000 | 49860 ± 556 | 249 |

EXAMPLE 3

$K_m$ of substrate for acid phosphatase for a variety of cells

TABLE 8

| Cell line | Source | Tissue type | Growth medium | BBTP (nM) & incubation time (at RT) |
|---|---|---|---|---|
| NIH 3T3 | ATCC | mouse embryonic fibroblasts | DMEM + 10% FBS | 0.5 mM, 1 $K_m$ = 87 $\mu$M |
| CHO-K1 | ATCC | Chinese hamster ovary | Ham'a F12 + 10% FBS | 0.5 mM, 1 h $K_m$ = 172 $\mu$M |
| HUVEC | Clonetics | human umbilical vein endothelial | Clonetics EGM | 0.5 mM, 1 h $K_m$ = 88 $\mu$M |
| HDMEC | Cell Applications | human dermal microvascular enodthelial | Clonetics EGM | 1.5 mM, 1 h $K_m$ = 80 $\mu$M |
| A431 | ATCC | human epidermal carcinoma | DMEM + 10% FBS | 1 mM, 45 m |
| T47-D | ATCC | human breast carcinoma | RPMI + 10% FBS | 1.5 mM, 1 h $K_m$ = 261 $\mu$M |

TABLE 8-continued

| Cell line | Source | Tissue type | Growth medium | BBTP (nM) & incubation time (at RT) |
|---|---|---|---|---|
| K562 suspension | ATCC | human chronic myelogenous leukemia | RPMI + 10% FBS | 1 mM, 1 h $K_m = 82\ \mu M$ |
| HL-60 suspension | ATCC | human promyelocytic leukemia | RPMI + 10% FBS | 1 mM, 1 h $K_m = 108\ \mu M$ |
| 2008 | ATCC | human ovarian carcinoma | RPMI + 10% FBS | 1 mM, 1 h $K_m = 106\ \mu M$ |
| Molt-4 suspension | ATCC | human acute lymphoblastic leukemia | RPMI + 10% FBS | 1 mM, 1 h $K_m = 130\ \mu M$ |

The $K_m$ for p-nitrophenyl phosphate of fetal bovine aortic endothelial cells was previously reported to be about 1 mM (see, Connolly et al. (1986) *Anal. Biochem.* 152:136–140).

Since modifications will be apparent to those of skill in this art, it is intended that this invention be limited only by the scope of the appended claims.

What is claimed is:

1. A method for measuring cell number, relative cell number or changes in cell number, comprising:
   incubating a cell lysate at acid pH with a benzothiazole substrate;
   raising the pH above 7; and
   measuring fluorescence, whereby the number of cells or relative number of cells or change in the number of cells is determined,
   wherein, the benzothiazole substrate has formula:

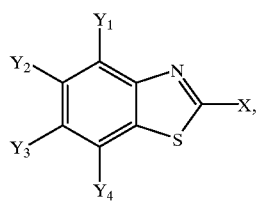

at least one of $Y_1$, $Y_2$, $Y_3$ and $Y_4$ is —A—W and the others are hydrogen in which A is an ionizable anion group and W is a fluorescence inhibiting group, A and W are linked by a bond that is cleavable by acid phosphatase; and
   X is a chemical moiety that contains at least two atoms that extends the resonance of the benzothiazole ring, with the proviso that X is not optionally substituted thiazolyl,
   whereby upon cleavage of the bond between the anion group and the fluorescence inhibiting group by the phosphatase yields a fluorescent product.

2. The method of claim 1, wherein X is —O—P(O)(OH)$_2$.

3. The method of claim 1, wherein X is selected from the group consisting of cyano, carbamoyl and 2-benzothiazolyl.

4. The method of claim 1, wherein the benzothiazole substrate is selected from the group consisting of 2-carbamoyl-6-hydroxybenzo-thiazole phosphate (ABTP), 2'(2-benzothiazoyl)-6'-hydroxy-benzthiazole phosphate (BBTP) and 2-cyano-6-hydroxybenzothiazole phosphate (CBTP).

5. The method of claim 1, wherein the incubation is effected at about 18° C. to 25° C.

6. The method of claim 1, wherein the cells are endothelial cells.

7. The method of claim 1, wherein the acid pH is between about 5 up to about 7, and the basic pH is between about 8 and 11.

8. The method of claim 1, wherein the basic pH is between about 9 and 11.

9. The method of claim 1, wherein endogenous acid phosphatase is measured.

10. The method of claim 1, wherein the substrate is 2'(2-benzothiazoyl)-6'-hydroxy-benzthiazole phosphate (BBTP).

11. The method of claim 1, wherein cell number, relative cell number or change in cell number is determined by correlating the measured fluorescence with cell number by comparing with a control standard of known cell number.

12. A method for screening for compounds that modulate cell proliferation, comprising:
   contacting the cells with a test compound,
   detecting the number of cells, relative number of cells or change in the number of cells, by a method comprising:
   incubating a cell lysate at acid pH with a benzothiazole;
   raising the pH above 7; and
   measuring fluorescence, whereby the number of cells or relative number of cells or change in the number of cells is determined,
   wherein, the benzothiazole substrate has formula:

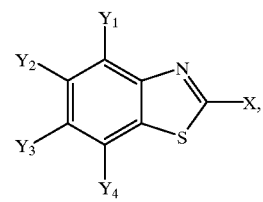

at least one of $Y_1$, $Y_2$, $Y_3$ and $Y_4$ is —A—W and the others are hydrogen in which A is an ionizable anion group and W is a fluorescence inhibiting group, A and W are linked by a bond that is cleavable by acid phosphatase; and
   X is a chemical moiety that contains at least two atoms that extends the resonance of the benzothiazole ring, with the proviso that X is not optionally substituted thiazolyl,
   whereby upon cleavage of the bond between the anion group and the fluorescence inhibiting group by the phosphatase yields a fluorescent product; and
   identifying compounds that alter the number of cells compared to a known modulator or in the absence of the compound.

13. The method of claim 12, wherein prior to, simultaneously with or after contacting the test compound, the cells are contacted with a compound known to modulate cell proliferation.

14. The method of claim 13, wherein the known compound stimulates cell proliferation.

15. The method of claim 12, wherein the cells are endothelial cells.

16. The method of claim 12, wherein the method screens for compounds that modulate angiogenesis.

17. The method of claim 12, wherein the method screens for compounds that inhibit angiogenesis.

18. The method of claim 17, wherein prior to, simultaneously with or after contacting the test compound, contacting the cells with a test compound the cells are contacted with a known angiogenesis stimulator.

19. The method of claim 18, wherein the known stimulator is a growth factor.

20. The method of claim 19, wherein the growth factor is selected from the group consisting of acidic fibroblast growth factor (FGF), basic FGF, epidermal growth factor (EGF) and , vascular endothelial growth factor (VEGF).

21. The method of claim 12, wherein the benzothiazole substrate is selected from the group consisting of 2-carbamoyl-6-hydroxybenzo-thiazole phosphate (ABTP), 2'(2-benzothiazoyl)-6'-hydroxy-benzthiazole phosphate (BBTP) and 2-cyano-6-hydroxybenzothiazole phosphate (CBTP).

22. The method of claim 12, wherein the substrate is 2'(2-benzothiazoyl)-6'-hydroxy-benzthiazole phosphate (BBTP).

23. The method of claim 12, wherein cell number, relative cell number or change in cell number is determined by correlating the measured fluorescence with cell number by comparing with a control standard of known cell number.

24. A method for screening for drugs for modulating cell proliferation, comprising:

contacting a plurality of recombinant cells with a test compound for a predetermined time;

wherein each recombinant cell of the plurality of recombinant cells comprises a reporter gene construct containing a reporter gene that encodes acid phosphatase in operative linkage with one or more transcriptional control elements that is regulated by a cell receptor; and measuring a level of phosphatase activity by contacting cell medium, if the phosphatase is secreted, or cell lysate, if the phosphatase is not secreted, with a benzothiazole substrate, and measuring fluorescence, wherein the fluorescence is proportional to cellular inhibition or stimulation by the test compound;

wherein the substrate has formula:

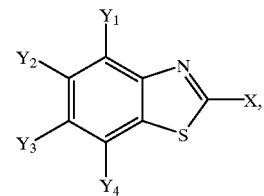

at least one of $Y_1$, $Y_2$, $Y_3$ and $Y_4$ is —A—W and the others are hydrogen in which A is an ionizable anion group and W is a fluorescence inhibiting group, A and W are linked by a bond that is cleavable by acid phosphatase; and X is a chemical moiety that contains at least two atoms that extends the resonance of the benzothiazole ring, with the proviso that X is not optionally substituted thiazolyl.

25. The method of claim 24, wherein the benzothiazole substrate is selected from the group consisting of 2-carbamoyl-6-hydroxybenzo-thiazole phosphate (ABTP), 2'(2-benzothiazoyl)-6'-hydroxy-benzthiazole phosphate (BBTP) and 2-cyano-6-hydroxybenzothiazole phosphate (CBTP).

26. The method of claim 25, wherein the substrate is 2'(2-benzothiazoyl)-6'-hydroxy-benzthiazole phosphate (BBTP).

* * * * *